United States Patent [19]

Williams

[11] 4,455,704
[45] Jun. 26, 1984

[54] TOOTHBRUSH AND TONGUE CLEANER

[76] Inventor: Robert L. Williams, 829 W. Olive Ave., Apt. A, Monrovia, Calif. 91016

[21] Appl. No.: 403,402

[22] Filed: Jul. 30, 1982

[51] Int. Cl.³ .................... A47L 13/50; A47L 13/12
[52] U.S. Cl. .................................. 15/111; 128/304; 15/236 R
[58] Field of Search .................. 15/111, 236, 167 R, 15/167 A; 128/304, 62 A; 132/84 R

[56] References Cited

U.S. PATENT DOCUMENTS

| | | | |
|---|---|---|---|
| 1,018,518 | 2/1912 | Pettit | 128/304 X |
| 1,741,143 | 12/1929 | Chin | 15/111 |
| 2,083,217 | 6/1937 | Brothers et al. | 15/111 |
| 2,574,654 | 11/1951 | Moore | 15/111 X |

FOREIGN PATENT DOCUMENTS 341008  3/1904  France ................................. 15/111

Primary Examiner—Peter Feldman
Attorney, Agent, or Firm—J. L. Jones, Sr.

[57] ABSTRACT

A conventional tooth brush is combined with a tongue cleaner as a single instrument, adapted to provide cooperative improved personal user hygiene. A tooth brush has a handle integrally extending coextensively from the conventional tooth brush bristle segment, the opposed handle terminating in an integral arcuate tongue scraper member, centrally secured on the arcuate structure curve at the opposed handle terminus. The arcuate scraper member can also be formed to be removable from the tooth brush handle. The terminal arcuate scraper structure is provided to the tooth brush user to scrape the user's top tongue surface, removing food particles and the like which can decay and provide offensive odors and tooth decay agents. The tooth brush user can wash the user's teeth with conventional tooth cleaner material in the conventional manner, then reverse the tooth brush in their hand and scrape the top surface of the user's tongue, further removing food particles and the like. The tooth brush and scraper combination is then washed for re-use, if required. The invention provides cooperative single instrumentation for the oral cleaning process.

4 Claims, 4 Drawing Figures

TOOTHBRUSH AND TONGUE CLEANER

BACKGROUND OF THE INVENTION

The tooth brush and tongue cleaner of this invention is classified in class 30, subclass 22, class 15/111, and class 128/304.

Peterkin el al disclose a tooth brush and spoon in U.S. Pat. No. 2,028,519, issued Jan. 21, 1936. A medicine spoon is disposed on the end of a tooth brush handle having a spoon bowl open top and lying in a plane parallel to the top of the brush bristles, providing a combination of a tooth brush for the mouth and a spoon for taking medicine or the like.

Yao et al disclose in U.S. Pat. No. 3,254,356, issued June 7, 1966, a tooth brush, tongue scraper and ear cleaner combination.

In U.S. Pat. No. 2,651,068, issued Sept. 8, 1953, Seko discloses a tooth brush and tongue scraper combination. The tongue scraper is a ring shaped member securing to the tooth brush handle opposed to the brush supporting member.

In U.S. Pat. No. 2,405,029, issued July 30, 1946, Gallanty et al disclose a tooth brush and tongue cleaning device combination. The tongue cleaner comprises a handle portion of the brush formed into a hook-shaped end, the hook-shaped end being of lesser width than a normal tongue and having a crescent shaped recess disposed in the hook shaped end.

A design patent U.S. Pat. No. Des. 122,815, issued Oct. 1, 1940 to Crosby, discloses a tooth brush and tongue cleaner combination having a closed continuous loop disposed in the brush handle opposed to the bristle configuration of the tooth brush. The continuous loop is applied as a tongue cleaner and scraper.

Cooke discloses in U.S. Pat. No. 1,860,924, issued May 31, 1932, a tooth brush and tongue scraper combination having a narrow hook shaped scraper disposed at the brush end opposed to the tooth brush bristles.

SUMMARY OF THE INVENTION

A conventional tooth brush is integrally combined with a top tongue scraper and cleaner, adaptively providing improved dental hygiene to the general public person using the combination with a conventional tooth cleaning composition. Specifically, the above combination has a single tooth brush handle, a coextensive conventional tooth brush bristle segment terminating a first combination terminus, and a coextensive integral arcuate tongue scraper segment centrally disposed and secured at the arcuate scraper arc mid-section to the second combination terminus of the tooth brush handle. The arcuate tongue scraper is adaptively sized and arcuately shaped to scrape the top surface of the user's tongue, having a blunt edge on the arcuate scraper blade, adapted to scrape the tongue top surface without cutting or abrading the tongue top surface. The arcuate tongue scraper can typically have a crescent shape arc extending one and one-quarter inch across the crescent shape, tip to crescent tip, or the like length. The arcuate tongue scraper crescent segment is integrally secured to the tooth brush handle at the mid-arc of the crescent shape segment disposed oppositely opposed to the tooth brush bristle segment. The arcuate tongue scraper can also be removably secured to the second handle terminus of a conventional tooth brush, utilizing an elastomeric socket member disposed mid-arc on the crescent shape of the tongue scraper, the socket member elastically gripping the conventional second terminus handle of a tooth brush. The interior of any arc modification is proportionally shaped in cross-section to provide a blunted cross-section edge which comfortably scrapes a user's tongue without cutting or abrading the user's tongue, as the scraper is moved over the top of the user's tongue.

Included in the objects of this invention are:

To provide a combination tooth brush and tongue cleaner in an integral entity which is readily available in a dental hygiene personal program.

To provide a simple, integral tooth brush and tongue cleaner combination which can be purchased by the general public and used in a dental hygiene program.

To provide a tongue cleaner device which can be simply secured to a conventional tooth brush handle.

To provide an inexpensive combination tooth brush and tongue cleaner for personal use by a member of the general public, enabling the public member to easily clean their teeth and the top of their tongue where food can accumulate and decay.

Other objects and advantages of this invention are taught in the following description and claims.

BRIEF DESCRIPTION OF THE DRAWINGS

The description of this invention is to be read in conjunction with the following drawings.

DESCRIPTION OF THE PREFERRED EMBODIMENT OF THE INVENTION

Figure 1:
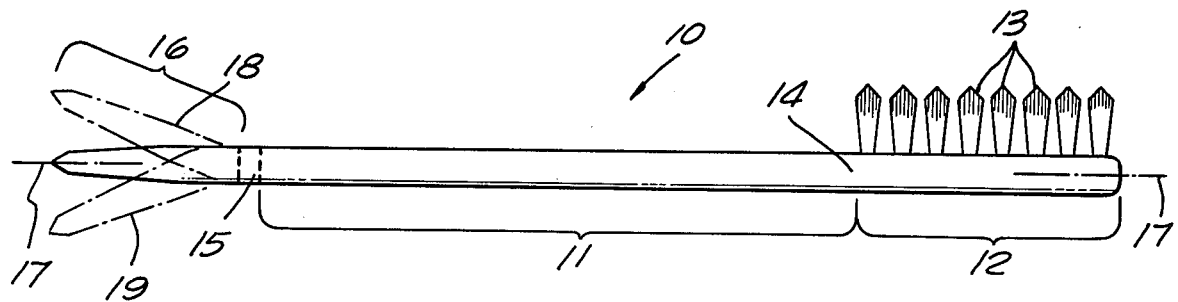
FIG. 1 is a side elevational view of the integral combination tooth brush and tongue scraper, with modified tongue scrapers shown in dotted lines.
Figure 2:
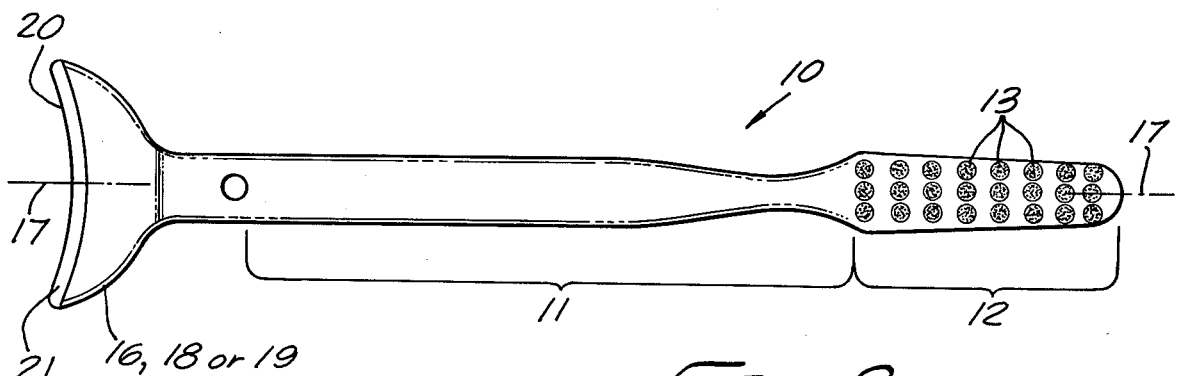
FIG. 2 is a top plan view of the integral combination tooth brush and tongue scraper of FIG. 1.

Referring to FIGS. 1 and 2 in detail, the side elevational view of the tooth brush and tongue cleaner combination 10, FIG. 1, has a tooth brush handle 11 extending a typical length of 5-9 inches with an integral coextensive conventional tooth brush bristle segment 12 having conventional multiple brush bristles 13 extending upward from segment 12. The tooth brush handle 11 has a first brush handle terminus 14 and a second brush handle terminus 15. An integral crescent shaped arcuate tongue scraper member 16 is illustrated in FIGS. 1 and 2, shown coextensively integrally secured at the crescent mid-arc to the second brush handle terminus 15. The tongue scraper member 16 is shown in FIG. 1 to extend straight along the axis 17 of the handle 11, in a first modification, then upward in the direction of the brush bristles 13 in a second modification 18, and finally downward in the direction away from the brush bristles 13 in the third scraper modification 19. As shown in FIG. 1, the tongue scraper member 16, and 18, and 19 extends at an include angle of not more than 60° to the second handle terminus 15.

FIG. 2 illustrates in a plan view the integral crescent shaped arcuate tongue scraper 16, and 18, and 19 disposed and integrally secured to the second brush handle terminus 15, as an extension which is centrally disposed along the arcuate crescent shape 16. The tongue scraper 16, and 18, and 19, each have an interior crescent shape arc 20, which has a suitable dull knife edge 21, extending the length of the crescent arc 20 and adapted and sized to clean the top surface of the human tongue where food and debris can incubate and decay. The dull knife edge 21 is coplanar along the entire length of the interior crescent shape are 20. The tongue scraper member 16, and 18, and 19 gradually tapers along its length from the end of the second brush handle terminus 15 to the dull knife edge 21. The dull knife edge 21 can be operated by the tooth brush and scraper user to remove food and the like from the tongue during a tooth brushing session, cleaning without injuring or cutting the user's tongue. Removing food debris can decrease the probability of the user having bad breath due to decaying food particles.

Figure 3:
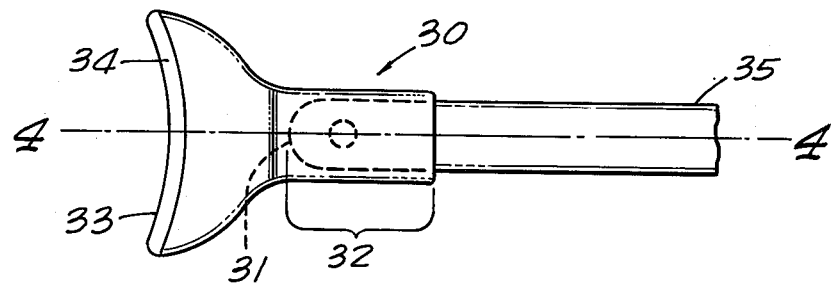
FIG. 3 is another modification of the tongue scraper, adapted to elastically secure on the second terminus of a tooth brush handle opposed to the first bristle terminus of the brush, dotted lines illustrating the attachment of FIG. 3 to a second terminus of a tooth brush handle.
Figure 4:
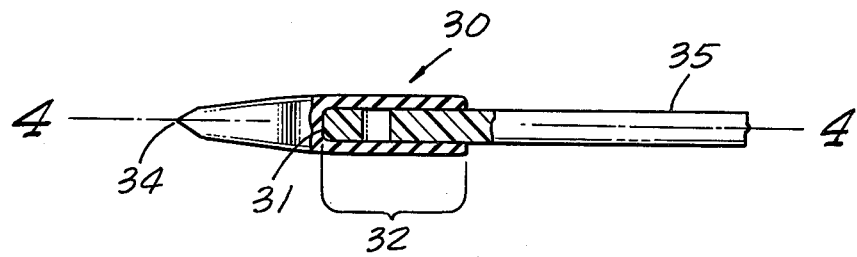
FIG. 4 is another view of FIG. 3 as rotated through 90° and taken along the axis of 4—4.

FIGS. 3 and 4 illustrate a further modification of a tongue scraper 30 which can be separately manufactured and secured by the user to any handle 35 of a standard tooth brush at a tooth brush second terminus 31, which is opposite to the conventional tooth brush bristle segment (not shown). The scraper 30 can be formed by a standard molding process from an elastomeric composition, such as a soft rubber, low density polyethylene, or the like, which will snugly elastically grip the tooth brush second terminus 31 and environs in a glovelike tight socket at 32, the soft compositions having a typical shore hardness of 40–80. The scraper 30 has an arcuate crescent shape, as in FIG. 2, the interior arc 33 has a dull knife edge 34 shown in cross section in FIG. 4. Again the dull knife edge 34 can be applied to a user's tongue to scrape off food debris and the like.

Other means than an elastomeric socket grip may be utilized to secure scraper 30 and the like, in further securing a modifications of grip 32, such as by a pinning means utilizing a pin, screw or the like.

The brush rigid structure of 10, such as 11, 12 and 16, can be a molded polyethylene, polypropylene, cellulose acetate, or the like inexpensive plastic composition.

Many modifications in the tooth brush and tongue cleaner can be made in the light of my teachings. It is understood that within the scope of the claims, the invention can be practiced otherwise than as described.

I claim:

1. A toothbrush and tongue cleaner combination comprising:
a linear tooth brush handle having a first brush handle terminus and
    a second brush handle terminus, said handle adapted and sized for human hand manipulation,
a conventional tooth brush bristle segment having multiple cleaning brush bristles disposed in said first brush handle terminus, said bristle segment integrally secured to said first brush handle terminus,
an integral crescent shaped arcuate tongue scraper member
    centrally disposed and secured at the arcuate structure mid-curve to the opposed second brush handle terminus at an included angle of not more than 60° to said second handle terminus, the tongue scraper interior arc of the crescent shaped scraper having a dull scraping edge sized and adapted to clean the top surface of a human tongue, said dull scraping edge being coplanar along the entire length of the crescent shaped interior arc, said scraper member gradually tapering along its length from the end of the second brush handle terminus to said dull knife edge,
said brush bristle segment adapted to brushing teeth and said
    scraper member adapted only to scraping the user's tongue top surface.

2. In the tooth brush and tongue cleaner combination of claim 1, the further modification wherein,
    said integral arcuate crescent shaped tongue scraper, secured at the arcuate mid-curve to the opposed second brush handle terminus, is disposed upwardly adjacent to the cleaning brush bristles of said first brush segment.

3. In the tooth brush and tongue cleaner combination of claim 1, the further modification wherein,
    said integral arcuate crescent shaped tongue scraper, secured at the arcuate mid-curve to the opposed second brush handle terminus, is disposed downwardly opposed to the cleaning brush bristles of said first brush segment.

4. A tongue cleaner adapted for use with a conventional tooth brush having a bristle segment on a first terminus of a brush handle and an opposed second brush handle terminus, comprising:
    a crescent shaped arcuate tongue scraper member having an interior arc on the crescent shape, with a dull knife scraping edge at said interior arc sized and adapted to clean the top surface of a human tongue, said tongue scraper member having a fastener segment adaptively sized and shaped to secure the scraper member at said member mid-arc to the second bristle handle terminus of the conventional toothbrush said tongue scraper member being disposed and secured at an included angle of not more than 60° to said second brush handle terminus, said dull scraping edge being coplanar along the entire length of the crescent shaped interior arc, and said scraper member gradually tapering along its length from the end of the second brush handle terminus to said dull knife scraping edge.

* * * * *